United States Patent [19]

Oloff et al.

[11] Patent Number: 5,071,657
[45] Date of Patent: Dec. 10, 1991

[54] DEVICE FOR TRANSDERMAL ADMINISTRATION OF ACTIVE MEDICINAL AGENTS

[75] Inventors: Horst Oloff; Johannes-Wilhelm Tack; Fred Windt; Ingfried Zimmermann, all of Berlin, Fed. Rep. of Germany

[73] Assignee: Schering Aktiengesellschaft, Berlin and Bergkamen, Fed. Rep. of Germany

[21] Appl. No.: 575,739

[22] Filed: Aug. 31, 1990

Related U.S. Application Data

[63] Continuation of Ser. No. 363,799, Jun. 9, 1989, abandoned, which is a continuation of Ser. No. 240,666, Sep. 6, 1988, abandoned, which is a continuation of Ser. No. 58,727, Jun. 5, 1987, abandoned, which is a continuation of Ser. No. 649,578, Sep. 12, 1984, abandoned.

[30] Foreign Application Priority Data

Sep. 12, 1983 [DE] Fed. Rep. of Germany ....... 3333240

[51] Int. Cl.$^5$ .......................... A61K 9/14; A61K 31/74
[52] U.S. Cl. ............................. 424/486; 424/DIG. 7; 514/944; 514/945; 604/304; 536/98
[58] Field of Search .................. 424/486, 78, DIG. 7; 514/944, 945; 604/304; 536/98

[56] References Cited

U.S. PATENT DOCUMENTS 3,598,123 8/1971 Zaffaroni ............................ 424/435

Primary Examiner—Nathan M. Nutter
Attorney, Agent, or Firm—Millen, White & Zelano

[57] ABSTRACT

A device for transdermal administration of active medicinal agents is based on the active medicinal agent dissolved to an extent of at least 50% in a nonflowable, physiologically acceptable gel, which latter is distributed in a microdisperse mode in a crosslinked silicone elastomer.

23 Claims, No Drawings

DEVICE FOR TRANSDERMAL ADMINISTRATION OF ACTIVE MEDICINAL AGENTS

This is a continuation of application Ser. No. 07/363,799, filed June 9, 1989, and now abandoned which is a continuation of application Ser. No. 07/240,666, filed Sept. 6, 1988 (abandoned), which is a continuation of application Ser. No. 07/058,727, filed June 5, 1987 (abandoned), which is a continuation of Ser. No. 06/649,578, filed Sept. 12, 1984 (abandoned).

BACKGROUND OF THE INVENTION

The present invention relates to a new agent and method for transdermal administration of medicaments.

It is known that the bioavailability of active medicinal agents administered orally or intravenously is frequently unsatisfactory. In recent years, attempts have therefore been made to improve the bioavailability of the active medicinal agents by transdermal administration. Thus, a device for transdermal administration of glyceryl trinitrate has been described, for example, in German Unexamined Laid-Open Application 3,131,610. However, this device is unsuitable for transdermal administration of solid medicines of low water solubility since the diffusion rate of such active agents is too low in such a device.

SUMMARY OF THE INVENTION

Thus, it is an object of this invention to provide a new, improved device or agent for transdermal administration of pharmacologically active compounds.

Other objects of this invention will be apparent to those skilled in the art to which this invention pertains.

These objects have been achieved by providing a device for transdermal administration of active medicinal agents, wherein the active medicinal agent is dissolved to at least 50% in a nonflowable, physiologically acceptable gel present in microdisperse distribution in a crosslinked silicone elastomer.

DETAILED DISCUSSION

In contrast to the prior art, the device of this invention is very well suited for transdermal administration of even solid drugs having low water solubility, e.g., in the range of about 5% or lower.

Suitable active medicinal agents which can be dissolved in the gel include, for example, compounds active as analgesic-antirheumatics, e.g., with ulcerogenic side effects, antibiotics, ergot compounds, β-receptor blockers, prostaglandins, prostacyclins, cardioactive glycosides, pharmacologically active peptides, especially steroid hormones, and many others.

Suitable analgesic-antirheumatic agents include, for example, phenylbutazone, oxyphenbutazone, indomethacin, naproxen, ibuprofen, etc. Suitable antibiotics include, inter alia, the penicillins, tetracyclines, streptomycins, etc. Suitable β-receptor blockers include, for example, pindolol, mepindolol, propranolol, etc. Suitable prostaglandins or prostacyclins include, for example, iloprost or nileprost, etc. Suitable cardioactive glycosides include, for example, the digitalis glycosides or the strophanthins, etc. Suitable pharmacologically active peptides include, inter alia, the gonadotropin-active peptides, e.g., LH-RH, etc.

Suitable steroid hormones especially include the sexual hormones having estrogenic, progestational, androgenic, or anabolic effects, such as estrogen, estradiol and their esters, e.g., the valerate, benzoate, or undecylate, ethinylestradiol, etc.; progestogens, such as norethisterone acetate, levonorgestrel, chlormadinone acetate, cyproterone acetate, desogestrel, or gestodene, etc.; androgens, such as testosterone and its esters (propionate, undecylate, etc.), etc.; anabolics, such as methandrostenolone, nandrolone and its esters, etc.; etc.

In general any pharmacologically active compound can be administered using the device of this invention as long as it is compatible with the composition of this invention and with transdermal application. The latter term has its conventional meaning herein; see, e.g., Drug Devel. and Ind. Pharm. 9, 1983, Vol. 4. With a transdermal system, the drug is absorbed from the skin into the capillaries that run under the skin and then into the general circulation.

The amount of active medicinal agent contained in the device is, of course, dependent on the desired dosage and on its effectiveness and absorbability and must be determined in each individual case, as is fully conventional using the usual preliminary routine testing and considerations. The amount of active material will be controlled by variation of its concentration in the gel component and by variation of the amount of gel dispersed in the silicone elastomer.

Without intending to limit this invention in any way, typical concentrations of the active agent in the gel will generally be about 50-80 wt %, and typical amounts of the total gel component in the elastomer will be about 25-75 wt %, preferably about 25-50 wt %. All percentages are based on the total composition involved. The lower value of about 50% is generally due to consideration of the minimum practical duration of administration which can be used.

Active medicinal agents readily soluble in water can be dissolved in gels comprising water and a thickener which forms a gel. Since the device of this invention is preferably intended for transdermal administration of medicines having low water solubility, the gel used for dissolving the active ingredient preferably comprises a thickener, a physiologically acceptable, high-boiling (e.g., a boiling point of about 80° or higher) organic solvent and, optionally, water.

The optionally aqueous solvents must be sufficiently lipophilic to dissolve the medicine, but, on the other hand, they must also be adequately hydrophilic to provide the desired active agent transport through the skin. Suitable solvents include, for example, dimethylformamide or, preferably, polyhydric alcohols or polyvalent ethers. Examples for polyhydric alcohols or polyvalent ethers include: ethylene glycol, propylene glycol, glycerol, ethylene glycol monomethyl ether, ethylene glycol dimethyl ether, dimethylisosorbide (=3,6-dimethoxyfuro[3,2-b]furan), diethylene glycol and ethers thereof (Dr. Otto-Albrecht Neumüller: Römpps Chemie Lexikon, 7th ed., 1972, Franckh'sche Verlagshandlung [publishers], Stuttgart, Federal Republic of Germany (Römpp), 814, 815), or polyethylene glycols having a molecular weight of up to 600 ("Römpp", 2750, 2751). The hydrophilicity of the solvents can be increased by adding water. On the other hand, the lipophilic property of the solvent can be raised by adding nonpolar oils, e.g., the esters of long-chain fatty acids known under the name of "Cetiol" ("Römpp", 539). A suitable hydrophilic/lipophilic balance can be achieved by routine preliminary testing where necessary. Typical satisfactory HLB values are about 2-20, preferably 4-16.

The device of this invention, of course, can contain only anhydrous solvents if the thickener required for gel formation is swellable therein, such as, for example, carboxymethylcellulose in dimethylisosorbide. Otherwise, such an amount of water must be added to the solvent as to make swelling of the thickener possible. Typical amounts of water when present are about 5-40 wt %, precise amounts being readily determinable based on the details of this application.

Suitable thickeners (See, e.g., "Römpp", 3792) are the swelling agents customarily used for gel formation in galenic pharmacy. Examples of suitable thickeners include: natural organic thickeners, such as agar-agar, gelatin, gum arabic, a pectin, etc., modified organic natural compounds, such as carboxymethylcellulose or cellulose ethers, or fully synthetic organic thickeners, such as polyacrylic compounds, vinyl polymers, or polyethers. Especially preferred thickeners are, for example, "Carbopol" [=TM of B.F. Goodrich, Chemical Company for water-soluble resins], e.g., for purely or partially aqueous systems, or carboxymethylcellulose.

The amount of thickener in the composition used to form the gel is conventionally dosed so that the thus-obtained gel is not flowable. Without intending to limit this invention, typical amounts of thickener in the gel-forming composition are about 5 wt % or less and of solvent or solvent mixture are routinely selected to achieve the function described herein. The term "non-flowable" herein functionally refers to the characteristic whereby the individual gel microparticles have a consistency whereby they change neither their position in the crosslinked silicone elastomer nor their shape.

Prior to incorporation into the device or agent of this invention, the gel-forming composition is conventionally treated to form the necessary gel and to set physiological pH where desired. See, e.g., B. W. Barry, Dermatological Formulations, Marcel Decker, Inc., N.Y., 1983, e.g., 296-351, which disclosure is incorporated by reference herein.

While the gel containing the active medicinal agent comprises the internal phase of the device of this invention, the external phase of the device comprises a conventional, crosslinked silicone elastomer. Preferably, an addition-crosslinked RTV system is utilized as the silicone elastomer, but this does not exclude the possibility of also using condensation-crosslinked RTV systems or any other compatible system. Bicomponent systems are preferred [Ullmanns Encyklopaedie der technischen Chemie, 4th ed., 21 (1982), catchword "Silicones," pp. 511 et seq.]. See also, Barry, supra, which disclosure is incorporated by reference herein. Suitable bicomponent systems, for example, comprise:

1-10% by weight of polydimethyl hydrogen siloxane having an average molecular weight of 300-2,000

1-10% by weight of 2,4,6,8-tetramethyl-2,4,6,8-tetravinylcyclotetrasiloxane 10-100 ppm of platinum catalyst and vinyl-group-terminated polydimethylsiloxane having an average molecular weight of 3,000-20,000

It is customary to form two components, the first containing the polydimethyl hydrogen siloxane and part of the vinyl-group-terminated polydimethysiloxane. The second component contains the remainder of the vinyl-group-terminated polydimethylsiloxane, the 2,4,6,8-tetramethyl-2,4,6,8-tetravinylcyclotetrasiloxane, and the catalyst. A suitable platinum catalyst is, for example, 2,4,6,8-tetramethyl-2,4,6,8-tetravinylcyclotetrasiloxanyl platinum.

The network chain length of all of the silicone elastomers can be varied within wide limits, by variation of the quantitative ratios of reactants, e.g., of polydimethyl hydrogen siloxane, vinyl-group-terminated polydimethylsiloxane, and 2,4,6,8-tetramethyl-2,4,6,8-tetravinylsiloxane, and by variation of the chain length of the reactants, e.g., polymethyl hydrogen siloxane and vinyl-group-terminated polydimethylsiloxane. This makes it possible to produce devices of this invention for the transdermal administration of active medicinal agents with differing diffusion coefficients, thus making available agents wherein an optimum release rate is achieved for the active ingredient.

The degree of crosslinking is determinable from a determination of the network chain length, since the network chain length is the molecular weight of the chain length between the crosslinking points. This is determined empirically. This value divided by the molecular weight of a siloxane unit is the degree of crosslinking. The empirical determination of the molecular weight between the cross-linking sites can be accomplished conventionally according to the method described in the publication by Treloar: The Physics of Rubber Elasticity—Clarendon Press Oxford, 1975, p. 142, which disclosure is incorporated by reference herein.

With increasing degree of crosslinking, the "free volume" in the network is diminished, and the diffusion resistance is increased. With routine preliminary experiment, the necessary degree of crosslinking to provide the the desired rate of administration (diffusion resistance) for a given system can be readily selected.

In general, it is practical to choose silicone elastomers having a network chain length of 20-500; especially in the case of steroid hormones, silicone elastomers are preferred having a network chain length of 50-250.

Methods and agents for crosslinking the silicone elastomer are all fully conventional and are discussed in the references discussed herein.

In order to produce the device of this invention, the blended elastomer components can be intimately mixed with one-third to three parts by weight of the gel containing the active medicinal agent, using any conventional technique whereby the gel phase is micro-dispersed, i.e., has a droplet size of about 5-500 $\mu$m. It is vulcanized at from 40° to 100° C., preferably in such a way that sheets are produced having a thickness of 0.5-5 mm.

The transport of active agent from the device of this invention (called "system" hereinbelow) through its external boundary surface in the direction toward the skin is caused by the concentration gradient Cis/Cas (Cis=concentration within, Cas=concentration outside of the system) and can be described as a function of the boundary surface A, the time t, the concentration Cis, and the diffusion coefficient D:

$$Q_t = f(A, t, Cis, D)$$

This macroscopic consideration is also valid for the microscopic description of the boundary surface of gel/silicone in the interior of the system. Because of the diffusion gradient, the active agent diffuses through the boundary surface A' of the internal phase toward the external phase in the direction of the external boundary of the system.

The diffusion coefficient $D'$ of the active agent in the external phase, the length of the diffusion route $l$, and the size of the boundary surfaces $A'$ between internal and external phases determine the transport of active agent within the system:

$$q_t = f(A', l, D')$$

The variable $A'$ is dependent on the droplet distribution in the system and can be readily influenced by incorporation parameters. By varying the ratio of $A'/A$ over a wide range, e.g., by droplet size and amount and by system size, e.g., 25–500, the active agent release of the system can thus be altered.

It is furthermore clear from the general functional description $$Q_t = f(A'/A, t, C_is, D'/D)$$

that a change in the release rate can be attained by varying the diffusion coefficient $D'$ (=diffusion within the system). The change in diffusion coefficient $D'$, as mentioned above, can be obtained by control of the structure of the silicone elastomer phase, e.g., by control of crosslinking degree.

The simple variability of factors $A'$ and $D'$ leads to a significant advantage over other systems: They represent mutually independent variables for adjusting the release rate of active agent, e.g., over the range of about 0.1 to about 500 mg per day, which range can readily be extended in either direction.

Packing and administration of the agent of this invention is fully conventional.

In order to produce plasters, it is possible, for example, to vulcanize disks of the device of this invention onto an aluminum-coated substrate film, provide this film with an adhesive (contact adhesive) around the device, and seal the arrangement with a protective film. Similarly, any other form of agent or device for transdermal application can be employed in connection with the invention by routine modification of the basic device described herein. See, e.g., Barry, supra, which disclosure is incorporated by reference herein.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

(A) Preparation of the Gel Phase Containing the Active Agent 300 mg of estradiol 17-valerate is dissolved in a mixture of 22.55 g of glycerol, 87% strength, with 22.55 g of dimethyl diglycol and 5.64 g of distilled water. The solution is thickened at room temperature under agitation with 1.13 g of "Carbopol" 934. To complete gel formation and to set physiological pH conditions, the pH is adjusted to 5.0 with about 1N sodium hydroxide solution.

(B) Preparation of the Silicone Elastomer Phase

In a reaction vessel with agitator which can be sealed to be vacuum-tight, 48.80 g of vinyl-group-terminated dimethylpolysiloxane (average molecular weight 6,000), 0.42 g of 2,4,6,8-tetramethyl-2,4,6,8-tetravinyltetracyclosiloxane, and 2.99 g of polydimethyl hydrogen siloxane having an average molecular weight of 350–500, and 15 ppm of platinum catalyst (in the form of a toluene solution of 2,4,6,8-tetramethyl-2,4,6,8-tetravinyltetracyclosiloxanyl platinum) are mixed together.

(C) Preparation of the Device for Transdermal Administration of Estradiol 17-Valerate The gel phase produced according to (A) is added to the silicone elastomer phase; the mixture is stirred under a vacuum (100 torr) for 20 minutes with 1,250 rpm. Then the thus-obtained dispersion is vulcanized in disk-shaped film molds having a surface of 10 cm² and a depth of 1.5 mm for one hour at 60° C.

EXAMPLE 2

(A) Preparation of the Gel Phase Containing the Active Agent 500 mg of testosterone is dissolved in a mixture of 8.5 g of dimethyl diglyol, 8.5 g of "Cetiol" HE, 4.0 g of distilled water, 20.0 g of glycerol, 87% strength, 1.0 g of polyglycol MG 400, and 3.0 ml of buffer solution, pH 9.0. The solution is thickened under agitation with 0.85 g of "Carbopol" 934.

(B) Preparation of the Silicone Elastomer Phase

In a reaction vessel with agitator which can be sealed to be vacuum-tight, 51.37 g of vinyl-group-terminated dimethylpolysiloxane (average molecular weight 6,000), 0.93 g of 2,4,6,8-tetramethyl-2,4,6,8-tetravinyltetracyclosiloxane, and 0.914 g of polydimethyl hydrogen siloxane having an average molecular weight of 350–500, and 15 ppm of platinum catalyst (in the form of a toluene solution of 2,4,6,8-tetramethyl-2,4,6,8-tetravinyltetracyclosiloxanyl platinum) are mixed together.

(C) Preparation of the Device for Transdermal Administration of Testosterone

The gel phase prepared as described in (A) is added to the silicone elastomer phase; the mixture is stirred under vacuum (100 torr) for 20 minutes with 1,250 rpm. Then the resultant dispersion is vulcanized in disk-shaped film molds having a surface of 10 cm² and a depth of 1.5 mm for one hour at 60° C.

EXAMPLE 3

(A) Preparation of the Gel Phase Containing the Active Agent 0.8 g of estradiol is dissolved in a mixture of 10.68 g of glycerol, anhydrous, 49.9 g of "Cetiol" HE, 8.93 g of distilled water. This solution is thickened under agitation with 1.84 g of "Carbopol" 934. In order to improve gel structure and to set physiological conditions, a pH of 5.0 is provided with approximately 1N sodium hydroxide solution.

(B) Preparation of the Silicone Elastomer Phase

In a reaction vessel with agitator, sealable to be vacuum-tight, 82.40 g of vinyl-group-terminated dimethylpolysiloxane (average molecular weight 6,000), 0.42 g of 2,4,6,8-tetramethyl-2,4,6,8-tetravinyltetracyclosiloxane, and 2.99 g of polydimethyl hydrogen siloxane with an average molecular weight of 350–500, and 15 ppm of platinum catalyst (in the form of a toluene solution of 2,4,6,8-tetramethyl-2,4,6,8-tetravinyltetracyclosiloxanyl platinum) are mixed together.

(C) Preparation of the Device for Transdermal Administration of Estradiol

The gel phase, prepared according to (A), is added to the silicone elastomer phase; the mixture is stirred for 20 minutes under vacuum (100 torr) at 1,250 rpm. Then the thus-obtained dispersion is vulcanized at 60° C. for one hour in disk-shaped film molds having a surface of 10 cm² and a depth of 0.9 mm.

EXAMPLE 4

(A) Preparation of the Gel Phase Containing the Active Agent

With slight heating (about 45° C.), 5.0 g of polyglycol MG 6000 is dissolved in a mixture of 5.0 g of distilled water, 5.0 g of glycerol, anhydrous, and 15.0 g of dimethyl diglycol.

After cooling, 0.1 g of microcrystalline lisuride base is incorporated into the solution; 30% of the active agent remain undissolved.

The mixture is thickened under agitation with 1.0 g of "Carbopol" 934 and adjusted to pH 5.0 with about 1N sodium hydroxide solution.

(B) Preparation of the Silicone Elastomer Phase

In a reaction vessel with agitator, sealable to be vacuum-tight, a mixture is prepared from 56.91 g of vinyl-group-terminated dimethylpolysiloxane (average molecular weight 6,000), 0.09 g of 2,4,6,8-tetramethyl-2,4,6,8-tetravinyltetracyclosiloxane, and 1.04 g of polydimethyl hydrogen siloxane having an average molecular weight of 350-500, and 15 ppm of platinum catalyst (in the form of a toluene solution of 2,4,6,8-tetramethyl-2,4,6,8-tetravinyltetracyclosiloxanyl platinum).

(C) Preparation of the Device for Transdermal Administration of Lisuride Base

The gel phase, prepared as described in (A), is added to the silicone elastomer phase; the mixture is agitated under vacuum (100 torr) for 20 minutes at 1,250 rpm. Then the resultant dispersion is vulcanized for one hour at 60° C. in disk-shaped film molds.

EXAMPLE 5

(A) Preparation of the Gel Phase Containing the Active Agent 2.76 g of estradiol is dissolved in 49.52 g of dimethylisosorbide (DMI, manufacturer: Atlas-Chemie, D-4300 Essen).

Under agitation, 2.72 g of hydroxypropylcellulose ("Klucel" GF) (manufacturer: Herkules GmbH, D-2050 Hamburg) is introduced into the solution. After 4 hours of agitation at room temperature, a gel is formed.

(B) Preparation of the Silicone Elastomer Phase

In a reaction vessel with agitator, sealable to be vacuum-tight, a mixture is prepared from 47.14 g of vinyl-group-terminated dimethylpolysiloxane (average molecular weight 6,000), 0.55 g of 2,4,6,8-tetramethyl-2,4,6,8-tetravinyltetracyclosiloxane, and 2.31 g of polydimethyl hydrogen siloxane with an average molecular weight of 350-500, and 15 ppm of platinum catalyst (in the form of a toluene solution of 2,4,6,8-tetramethyl-2,4,6,8-tetravinyltetracyclosiloxanyl platinum).

(C) Preparation of the Device for Transdermal Administration of Estradiol

The gel phase, prepared as set forth in (A), is added to the silicone elastomer phase; the mixture is stirred under vacuum (100 torr) for 20 minutes with 1,250 rpm. Then the resultant dispersion is vulcanized for one hour at 60° C. in disk-shaped film molds having a surface of 10 cm² and a depth of 0.5 mm.

EXAMPLE 6

The transdermal systems described in the examples above are applied, for example, to the inner side of the upper arm or to the chest and permitted to remain there during the intended period of administration. In Examples 3 and 5, for example, this period is 1 to 7 days, often 1 to 3 days.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An agent useful for transdermal administration of a pharmacologically active agent, comprising:
   (a) a matrix of a pharmacologically acceptable crosslinked, silicone elastomer, comprising:
      (i) 1–10% by weight of a polydimethylhydrogensiloxane having an average molecular weight of 300–2000;
      (ii) 1–10% by weight of a 2,4,6,8-tetramethyl-2,4,6,8-tetravinylcyclotetrasiloxane; and
      (iii) 10–100 ppm of platinum catalyst in a vinyl group-terminated polydimethylsiloxane having an average molecular weight of 3000–20,000;
   (b) a non-flowable, physiologically acceptable gel microdispersed in said matrix, wherein said gel is based on a combination of a gel-forming thickener, water, and a solvent which is a polyhydric alcohol or a polyvalent ether; and
   (c) an active agent dissolved in the microdispersed gel phase in a concentration of at least 50 wt. % based on the gel phase, wherein said matrix is in the form of a sheet having a thickness of 0.5 to 5 mm.

2. An agent of claim 1, wherein the active medicinal agent is a steroid hormone, an ergot compound, a β-receptor blocker, a prostaglandin, a prostacyclin, a cardioactive glycoside, or a pharmacologically active peptide.

3. An agent of claim 2, wherein the active medicinal agent is a steroid hormone.

4. An agent of claim 3, wherein the agent is an estradiol, norethisterone acetate, levonorgestrel, chlormadinone acetate, cyproterone acetate, desogestrel, gestodene, a testosterone, methandrostenolone or nandrolone.

5. An agent of claim 1 wherein said combination upon which the gel is based further comprises water.

6. An agent of claim 1, wherein the crosslinked silicone elastomer is an addition-crosslinked silicone RTV elastomer.

7. An agent of claim 1, wherein the crosslinked silicone elastomer has a network chain length of 20–500.

8. An agent of claim 7, wherein the crosslinked silicone elastomer has a network chain length of 50-250.

9. An agent of claim 1 wherein the solvent is ethylene glycol, propylene glycol, glycerol, ethylene gylcol monomethyl ether, ethylene glycol dimethyl ether, dimethylisosorbide, diethylene glycol, a diethylene glycol ether or a polyethylene glycol.

10. An agent of claim 1 wherein the thickener is agar-agar, gelatin, gum arabic, a pectin, cellulose, a ether, a polyacrylic compound, a vinyl polymer or a polyether.

11. An agent of claim 1 wherein the thickener is a Carbopol or carboxymethylcellulose.

12. An agent of claim 1 wherein the content of the gel component containing the active agent is 25-75 wt %.

13. An agent of claim 1 wherein the particle size of the gel is 5-500 μm.

14. A process for the preparation of an agent useful for transdermal administration of active medicinal agents according to claim 1, comprising suspending the active agent-containing gel in the components required for formation of the crosslinked silicone elastomer, and vulcanizing the thus-obtained suspension.

15. In a method of transdermally administering a pharmacologically active compound in an agent suitable for transdermal administration, the improvement wherein the agent is one of claim 1.

16. An agent of claim 1, wherein the active medicinal agent exhibits a water solubility of about 5% or lower.

17. An agent of claim 2, wherein the gel comprises a gel-forming thickener and an organic solvent having an HLB value from about 2-20.

18. An agent of claim 17, wherein the particle size of the gel is 5-500 μm.

19. An agent useful for transdermal administration of a pharmacologically active agent, comprising a solid, self-supporting matrix material having dispersed therein a gel with an active agent dissolved therein, wherein:
   said matrix comprises a pharmacologically acceptable, cross-linked, vulcanized silicone elastomer;
   said gel is physiologically acceptable and is microdispersed within said matrix at particle sizes of from 5-500 μm;
   said active agent is present in the gel phase at a concentration of at least 50 wt. % based on the gel phase; and
   said matrix material is in the form of a molded sheet having a thickness of 0.5 to 5 mm.

20. An agent of claim 19, wherein the gel is based on a combination of gel-forming thickener, water, and a solvent which is a polyhydric alcohol or a polyvalent ether.

21. An agent as in claim 19, which does not contain a backing layer.

22. An agent of claim 19, wherein the crosslinked silicone elastomer is prepared from a bicomponent system, comprising 1-10% by weight polydimethylhydrogensiloxane having an average molecular weight of 300-2000, 1-10% by weight of 2,4,6,8-tetramethyl-2,4,6,8-tetravinylchlorotetrasiloxane, and 10-100 ppm of platinum catalyst and vinyl group-terminated polydimethylsiloxane having an average molecular weight of 3000-20,000;
   wherein the thickener is agar, gelatin, gum arabic, a pectin, carboxymethyl-cellulose, a cellulose ether, a polyacrylic compound, a vinyl polymer, or a polyether;
   wherein the solvent is ethylene glycol, propylene glycol, glycerol, ethylene glycol monomethyl ether, ethylene glycol dimethyl ether, dimethyl isosorbide, diethylene glycol, diethylene glycol ethers, or polyethylene glycols; and
   wherein the active agent is estradiol, norethisterone acetate, levonorgestrel, chloromadinone, cyproterone acetate, desogestrel, gestodene, testosterones, methandrostenolone, or nondrolone.

23. An agent of claim 19, wherein the silicone elastomer is vulcanized at 40°-100 C.

* * * * *